US011252960B2

(12) United States Patent
Wenzel et al.

(10) Patent No.: US 11,252,960 B2
(45) Date of Patent: Feb. 22, 2022

(54) ANTIBACTERIAL COMPOSITION INCLUDING BENZOIC ACID ESTER AND METHODS OF INHIBITING BACTERIAL GROWTH UTILIZING THE SAME

(71) Applicant: KIMBERLY-CLARK WORLDWIDE, INC., Neenah, WI (US)

(72) Inventors: Scott W. Wenzel, Neenah, WI (US); Corey T. Cunningham, Larsen, WI (US); Andrew R. Kischnick, Appleton, WI (US); Vinod Chaudhary, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/478,273

(22) PCT Filed: Jan. 31, 2017

(86) PCT No.: PCT/US2017/015725
§ 371 (c)(1),
(2) Date: Jul. 16, 2019

(87) PCT Pub. No.: WO2018/143911
PCT Pub. Date: Aug. 9, 2018

(65) Prior Publication Data
US 2019/0357533 A1 Nov. 28, 2019

(51) Int. Cl.
*A01N 37/36* (2006.01)
*A01N 25/34* (2006.01)
*A01N 25/08* (2006.01)

(52) U.S. Cl.
CPC ............ *A01N 37/36* (2013.01); *A01N 25/08* (2013.01); *A01N 25/34* (2013.01)

(58) Field of Classification Search
None
See application file for complete search history.

(56) References Cited

U.S. PATENT DOCUMENTS

| | | |
|---|---|---|
| 598,648 A | 2/1898 | Schupphaus |
| 3,012,064 A | 12/1961 | Hertling et al. |
| 4,024,164 A | 5/1977 | Bailey et al. |
| 4,134,868 A | 1/1979 | Minagawa et al. |
| 4,223,160 A | 9/1980 | Hess |
| 4,278,655 A | 7/1981 | Elmi |
| 4,691,043 A | 9/1987 | Demame et al. |
| 5,081,287 A | 1/1992 | Peake et al. |
| 6,365,140 B1 | 4/2002 | Melby et al. |
| 6,413,529 B1 | 7/2002 | Beerse et al. |
| 6,447,793 B2 | 9/2002 | Aust et al. |
| 6,559,110 B1 | 5/2003 | Lopes |
| 6,569,463 B2 | 5/2003 | Patel et al. |
| 6,673,336 B2 | 1/2004 | Buchholz et al. |
| 6,706,276 B2 | 3/2004 | Garg et al. |
| 6,787,342 B2 | 9/2004 | Chen |
| 6,835,536 B2 | 12/2004 | Krieger et al. |
| 6,897,281 B2 | 5/2005 | Lubnin et al. |
| 6,946,427 B2 | 9/2005 | Lutz et al. |
| 7,128,923 B2 | 10/2006 | Patt |
| 7,342,044 B2 | 3/2008 | Lutz |
| 7,786,176 B2 | 8/2010 | Martin et al. |
| 7,795,203 B2 | 9/2010 | Babizhayev |
| 8,008,255 B2 | 8/2011 | Ong et al. |
| 8,097,584 B2 | 1/2012 | Poulsen |
| 8,226,965 B2 | 7/2012 | Baker, Jr. et al. |
| 8,227,393 B2 | 7/2012 | Fevola |
| 8,673,865 B2 | 3/2014 | Ueno et al. |
| 8,784,780 B2 | 7/2014 | Gurge et al. |
| 9,216,208 B2 | 12/2015 | Canonge et al. |
| 2003/0113387 A1 | 6/2003 | Tsuchida et al. |
| 2003/0152610 A1 | 8/2003 | Rolf et al. |
| 2003/0207884 A1 | 11/2003 | Haap et al. |
| 2004/0105894 A1 | 6/2004 | Gupta |
| 2005/0008601 A1 | 1/2005 | Ariotto et al. |
| 2006/0286053 A1 | 12/2006 | Dueva-Koganov et al. |
| 2007/0190005 A1 | 8/2007 | Rozsa et al. |
| 2008/0139672 A1 | 6/2008 | Rozsa et al. |
| 2008/0207481 A1 | 8/2008 | Meine et al. |
| 2008/0221003 A1 | 9/2008 | Meine et al. |
| 2008/0234173 A1 | 9/2008 | Warr et al. |

(Continued)

FOREIGN PATENT DOCUMENTS

| | | |
|---|---|---|
| CN | 1346263 A | 4/2002 |
| CN | 1411339 A | 4/2003 |

(Continued)

OTHER PUBLICATIONS

Annex V List of Preservatives Allowed in Cosmetic Products, published by the European Union Open Data Portal, Internet web page "http://ec.europa.eu/growth/tools-databases/cosing/pdf/COSING_Annex%20V_v2.pdf", Jan. 12, 2016, pp. 1-8.
Iscaguard Preservative Blends, 'Preservatives available from ISCA', Wales, UK, www.iscauk.com.
Abaee et al., 'Environmentally friendly transesterification and transcylation reactions under LiBr catalysis,' Springer, Jan. 28, 2009.
Chen et al., 'Facile oxidative cleavage fo benzylidene acetals using molecular oxygen catalyzed by N-hydroxyphthalimide/Co(Oac)2,' Tetrahedron Letters 42 (2001) 4955-4958.
Curini et al., 'Oxone®: A Convenient Reagent for the Oxidation of Acetals,' Synlett 1999, No. 6, 777-779.

(Continued)

*Primary Examiner* — Leslie A. Royds Draper
(74) *Attorney, Agent, or Firm* — Kimberly-Clark Worldwide, Inc.

(57) ABSTRACT

Antibacterial compositions and methods for inhibiting bacterial growth are disclosed. The antibacterial compositions can include a carrier and an antibacterial agent including a benzoic acid ester. The benzoic acid ester can have a carbon chain having a length of two to ten. The benzoic acid ester can have a hydroxyl group on the carbon chain.

15 Claims, No Drawings

(56) References Cited

U.S. PATENT DOCUMENTS

| | | |
|---|---|---|
| 2008/0260659 A1 | 10/2008 | Natsch |
| 2009/0035340 A1 | 2/2009 | Landa et al. |
| 2009/0185995 A1 | 7/2009 | Vochecowicz et al. |
| 2009/0269394 A1 | 10/2009 | Baker, Jr. et al. |
| 2009/0304799 A1 | 12/2009 | Baker, Jr. et al. |
| 2010/0092526 A1 | 4/2010 | Baker, Jr. et al. |
| 2010/0226983 A1 | 9/2010 | Sutcliffe et al. |
| 2011/0190129 A1 | 8/2011 | Bell et al. |
| 2012/0064136 A1 | 3/2012 | Baker, Jr. et al. |
| 2012/0289590 A1 | 11/2012 | Ritterman et al. |
| 2012/0289597 A1 | 11/2012 | Farber |
| 2013/0029933 A1 | 1/2013 | Schnitzler et al. |
| 2013/0085103 A1 | 4/2013 | Mohan et al. |
| 2013/0251644 A1 | 9/2013 | Majhi et al. |
| 2014/0004163 A1 | 1/2014 | Mundschau et al. |
| 2014/0335034 A1 | 11/2014 | Panandiker et al. |
| 2014/0335167 A1 | 11/2014 | Panandiker et al. |
| 2015/0065684 A1 | 3/2015 | Steinkasserer et al. |
| 2015/0328236 A1 | 11/2015 | Tadros |
| 2016/0000067 A1 | 1/2016 | Bell et al. |

FOREIGN PATENT DOCUMENTS

| | | |
|---|---|---|
| CN | 102083786 A | 6/2011 |
| CN | 103520066 B | 8/2016 |
| DE | 102011111624 A1 | 2/2013 |
| EP | 0231816 B1 | 5/1991 |
| EP | 1347091 B1 | 7/2006 |
| EP | 1891926 A1 | 2/2008 |
| EP | 2774481 B1 | 6/2018 |
| GB | 910004 A | 11/1962 |
| WO | 04075866 A1 | 9/2004 |
| WO | 07106561 A2 | 9/2007 |
| WO | 12018519 A1 | 2/2012 |
| WO | 14037553 A2 | 3/2014 |
| WO | 18068825 A1 | 4/2018 |

OTHER PUBLICATIONS

Diab et al., 'Supramolecular Catalyst for Aldehyde Hydrogenation and Tandem Hydroformylation-Hydrogenation,' Angew. Chem. Int. Ed. 2009, 48, 8022-8026.

Fischer, 'Uber die Wechselwirkung zwischen Ester—undAlkoholgruppen bei Gengenwart von Katalysatoren,' Eingegangen am Jun. 25, 1920.

Fujioka et al., 'One-pot synthesis of imidazolines from aldehydes: detailed study about solvents and substrates,' Tetrahedron 63 (2007) 638-643.

Gopinath et al., 'Tertabutylammonium Tribromide (TBATB)-MeOH: An Efficient Chemoselective Reagent for the Cleavage of tert-Butyldimethylsilyl (TBDMS) Ethers,' Organic Letters, 2000, vol. 2, No. 26, 4177-4180.

Hosokawa et al., 'Palladium (II)-catalysed Oxidative Ring Cleavage of Cyclic Acetals with t-Butyl Hydroperoxide: Preparation of Monoesters of Diols,' J. Chem. Soc., Chem. Commun., 1983.

Kitagawa et al., 'Sulfenamide Catalyzed Oxidation of Alcohols to the Corresponding Carbonyl Compounds with Anhydrous Chloramine-T,' Chem. Pharm. Bull., 2002, vol. 50, No. 9, 1276-1279.

Maki et al., 'A New Convenient Method for Selective Monobenzoylation of Diols,' Tetrahedron Letters 39 (1998) 5601-5604.

Satyanarayana et al., 'A Convenient One Pot Synthesis of Esters of Carboxylic Acids from Alkyl or Aryl Halides,' Synthetic Communications: An International Journal for Rapid Communication of Synthetic Organic Chemistry, 1990, 20:21, 3273-3276.

Sueda et al., 'Oxidative Ring Cleavage of Cyclic Acetals with Hypervalent tert-Butylperoxy-i3-iodanes,' Organic Letters, 2001, vol. 3, No. 15, 2387-2390.

Taniguchi et al., 'Deprotection of Tetrahydropyranyl Ethers with Montmorillonite K-10 Clay in Methanol,' Synlett, 1999, No. 8, 1247-1248.

Batovska et al., 'Evaluation of antibacterial activity of synthetic and aromatic monoacylglycerols,' Polish Journal of Microbiology, 2008, vol. 57, No. 3, pp. 261-265.

Park, Eun-Soo et al., 'Antimicrobial activity of phenol and benzoic acid derivatives,' International Biodeterioration & Biodegradation, Dec. 2001, vol. 47, No. 4, pp. 209-214.

ANTIBACTERIAL COMPOSITION INCLUDING BENZOIC ACID ESTER AND METHODS OF INHIBITING BACTERIAL GROWTH UTILIZING THE SAME

TECHNICAL FIELD

Disclosed are antibacterial compositions and methods of inhibiting bacterial growth. More specifically, disclosed is an antibacterial composition that includes an antibacterial agent including a benzoic acid ester and method of utilizing the same to inhibit bacterial growth. The antibacterial composition may be applied to or incorporated into articles such as wipes, or into ointments, lotions, creams, salves, aerosols, gels, suspensions, sprays, foams, washes, or the like.

BACKGROUND OF THE DISCLOSURE

Preservatives are an often utilized component in cosmetic, pharmaceutical, and personal care products to ensure that a product stays fresh on the shelf, doesn't experience spoilage, and remains free from bacterial growth. In particular, because personal care products may be used to directly contact skin or mucosa such as around body orifices where the potential for transfer of materials from the product to the consumer may be a concern, it is generally good practice to reduce contamination of the product in every possible way. The need to control microbiological growth in personal care products is particularly acute in water based products such as non-ionic oil-in-water emulsions and in pre-impregnated wipes such as wet wipes.

Multiple options for preservatives that prevent bacterial growth, such as formaldehyde donors or parabens, have existed throughout history and these preservatives were highly efficacious and allowed for relatively easy preservation of personal care products. Recently, traditional preservatives have been less desirable components in personal care products in view of new regulations and consumer perceptions, thus limiting the options for preserving and preventing bacterial growth in certain products.

Alternative preservatives, such as organic acids, have been explored and have become more frequently utilized in the cosmetic and personal care field. Examples of these preservatives would be sorbic acid and its salts, benzoic acid and its salts, p-anisic acid, and salicylic acid. While these salts are efficacious in cosmetic and personal care products, each carry limitations. Specifically, the organic acids tend to have an inherent odor and can therefore only be used in low concentrations without affecting the overall olfactory perception of the product. Additionally, organic acids are only efficacious in the acid form, and thus, formulations including organic acids can be limited to a very narrow and low pH range in which they are efficacious (generally pH 3.5-5.0). Another limitation is that organic acids have limited water solubility in the efficacious range. While raising the pH of the formulation to provide the salt form can increase their solubility in water, doing so inherently reduces the efficacy against microorganisms; thus making the product unprotected against spoilage and bacterial growth.

Thus, there remains a need for antibacterial compositions that include alternative organic acid derivatives that have lower odor, can be used in a composition over a wider pH range without losing efficacy against bacterial growth, and can have greater water solubility than the parent organic acids.

SUMMARY OF THE DISCLOSURE

In one aspect of the disclosure, a method for inhibiting bacterial growth in a product is provided. The method can include providing an antibacterial composition including an antibacterial agent. The antibacterial agent can include a benzoic acid ester with a carbon chain having a length of two to ten. The benzoic acid ester can further include a hydroxyl group on the carbon chain. The method can further include applying the antibacterial composition to the product to inhibit bacterial growth in the product.

In another aspect of the disclosure, an antibacterial composition is provided. The antibacterial composition can include a carrier, a surfactant, and an antibacterial agent. The antibacterial agent can include a benzoic acid ester. The benzoic acid ester can have a carbon chain and a terminal hydroxyl group on the carbon chain.

In yet another aspect of the disclosure, an antibacterial composition is provided. The antibacterial composition can include a carrier, a surfactant, and an antibacterial agent. The antibacterial agent can include a benzoic acid ester including a carbon chain and a hydroxyl group on the carbon chain. The benzoic acid ester can include a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans*, and *Aspergillus brasiliensis*. The antibacterial composition can be substantially free of a traditional preservative.

DETAILED DESCRIPTION OF THE DISCLOSURE

The present disclosure is directed to antibacterial compositions and methods of inhibiting bacterial growth in which the antibacterial compositions include a benzoic acid derivative. In particular, the disclosure is directed to antibacterial compositions and associated methods in which the antibacterial composition includes a benzoic acid ester having a carbon chain and a hydroxyl group on the carbon chain. The antibacterial compositions could be utilized in a variety of cosmetic, pharmaceutical, and other personal care products. Suitable products could include, but are not limited to: shampoo, conditioner, soaps, moisturizers, skin protective, skin restorative and skin strengthening products, hand sanitizers, skin and body cleansers, deodorants, sunscreens, lip balms, lip sticks and the like. These products could take a variety of forms including but not limited to water-thin liquids, aqueous solutions, gels, balms, lotions, ointments, suspensions, creams, milks, salves, ointments, pastes, powders, aerosols, sprays, mists, mousses, emulsions, oils, foams, washes, solid sticks, aerosols, water, oil or silicone solutions or emulsions, including water in oil, oil in water, silicone in water, water in silicone and the like. Additionally, as will be described in further detail below, the forms of these products may be used in conjunction with a substrate, such that the solution may be added to the substrate for delivery. Suitable substrate based products include, but are not limited to: wipes, facial tissue, bath tissue, paper towels, napkins, diapers, diaper pants, feminine hygiene products (tampons, pads), gloves, socks, masks or combinations thereof.

Within each of the above envisioned products, the benzoic acid esters could be used with a variety of ingredients utilized in cosmetic, pharmaceutical and other personal care products. Suitable ingredients, some of which will be described in further detail herein, can come from a broad category range including, but not limited to aqueous solvents, non-aqueous solvents, humectants, emollients, surfactants, emulsifiers, sequestrants, chelators, preservatives, pH modifiers, combinatorial preservatives/antimicrobial agents, disinfectants, colorants, rheology modifiers, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, deodorants, antiperspirants, fragrance, and various other optional ingredients as are known by one skilled in the art.

Antibacterial Agents

The antibacterial compositions of this disclosure include an antibacterial agent that is a derivative of benzoic acid. The first benzoic acid derivative that was explored included adding hydroxyl, polyols or sugars to the para-position of the benzoic acid. The following benzoic acid derivatives compounds were tested and compared against benzoic acid in terms of their solubility, pH dependency, and their minimum inhibitory concentration ("MIC") against various bacteria and fungi. The solubility values were produced following the Determination of Aqueous Solubility by Miniaturized Shake Flask Method as discussed herein. The pH dependency values were produced following the Determination of Dissociation Constant (pKa) by Potentiometric Titration Method as discussed herein. The MIC values were produced following the Anti-bacterial and Anti-fungal Minimum Inhibitory Concentration (MIC) Method as described herein.

TABLE 1

Testing results on water solubility, pH dependence, and MIC for various benzoic acid derivatives including hydroxyls, polyols, and sugars.

| # | Compound Name | Compound Structure | Solubility (wt %) | pKa | MIC (%) | | | | | |
|---|---|---|---|---|---|---|---|---|---|---|
| | | | | | *S. Aureus* | *E. coli* | *B. cepacia* | *P. aeruginosa* | *C. albicans* | *A. brasiliensis* |
| | benzoic acid | | 0.2981 | 4.2 | 0.068 | 0.07 | 0.034 | 0.068 | 0.137 | 0.137 |
| 1 | 4-(2-hydroxyethoxy) benzoic acid | 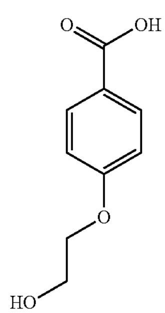 | 0.2779 | 4.95 | 0.041 | 0.165 | 0.082 | 0.082 | >0.165 | >0.165 |
| 2 | 4-(2,3-dihydroxypropoxy) benzoic acid | 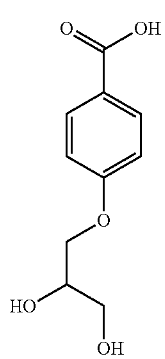 | 0.343 | 4.6 | 0.045 | 0.181 | 0.09 | 0.09 | >0.181 | >0.181 |

TABLE 1-continued

Testing results on water solubility, pH dependence, and MIC for various benzoic acid derivatives including hydroxyls, polyols, and sugars.

| | | | Solubility | | MIC (%) | | | | | |
|---|---|---|---|---|---|---|---|---|---|---|
| # | Compound Name | Compound Structure | (wt %) | pKa | S. Aureus | E. coli | B. cepacia | P. aeruginosa | C. albicans | A. brasiliensis |
| 3 | 4-{[(3R,4S,5R,6R)-3,4,5-trihydroxy-6-(hydroxymethyl)oxan-2-yl]oxy}benzoic acid | | >1.00 | 4.5 | >0.87 | >0.87 | >0.87 | >0.87 | >0.87 | >0.87 |
| 4 | 4-{[3,4-dihydroxy-5-(hydroxymethyl)oxolan-2-yl]oxy}benzoic acid | | >1.00 | 4.6 | 0.125 | 1 | 0.25 | 0.5 | >1 | >1 |
| 5 | 4-{[4-hydroxy-5-(hydroxymethyl)oxolan-2-yl]oxy}benzoic acid | | 0.11 | 5.6 | 0.017 | >0.069 | 0.034 | 0.034 | >0.069 | >0.069 |
| 6 | 4-(4-hydroxybutoxy)benzoic acid | | 0.0667 | 4.6 | 0.01 | 0.04 | 0.02 | 0.04 | >0.04 | >0.04 |

TABLE 1-continued

Testing results on water solubility, pH dependence, and MIC for various benzoic acid derivatives including hydroxyls, polyols, and sugars.

| # | Compound Name | Compound Structure | Solubility (wt %) | pKa | MIC (%) S. Aureus | E. coli | B. cepacia | P. aeruginosa | C. albicans | A. brasiliensis |
|---|---|---|---|---|---|---|---|---|---|---|
| 7 | 4-(2-hydroxypropoxy) benzoic acid | 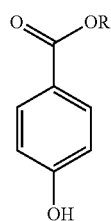 | 0.123 | 5.6 | 0.02 | 0.079 | 0.02 | 0.039 | >0.079 | >0.079 |

As can be seen in Table 1, benzoic acid derivatives including hydroxyls, polyols, and sugars provided varied results in terms of solubility, pH dependence, and MIC values in comparison to benzoic acid. Some molecules were more water soluble than Benzoic Acid, but were still pH dependent and/or had poor kill against bacteria. For example, compound #3 in Table 1 exhibited a water solubility of >1.00, but had a MIC value of >0.87 for each bacteria and fungi tested. Other molecules demonstrated poor water solubility values and/or demonstrated poor kill against at least some of the bacteria and fungi tested. As one example, compound #5 in Table 1 exhibited a water solubility of 0.11, and lower MIC values against *Escherichia coli* (*E. coli*), *Candida albicans* (*C. albicans*), and *Aspergillus brasiliensis* (*A. brasiliensis*) than the MIC values of benzoic acid against the same respective bacteria/fungi.

In contrast to aromatic carboxylic acids, such as benzoic acid, that have a COOH on the aromatic ring, aromatic esters are derived from carboxylic acids where the hydrogen in this group is replaced by a hydrocarbon group of some kind to obtain a COOR moiety on the aromatic ring. The hydrocarbon can vary, but one possibility is that it can be an alkyl group such as methyl, ethyl, propyl, isopropyl, butyl, isobutyl, and isodecyl. A benzoic acid ester of this type is different than the traditional class of preservatives called parabens. The chemical structure for parabens is shown here:

In contrast to parabens, benzoic acid esters are different in structure as they do not have a p-hydroxyl group on the aromatic ring. In some embodiments of the present disclosure, the benzoic acid esters can include a carbon chain. In preferred embodiments, as discussed further below, the benzoic acid esters can include a hydroxyl group (OH) on the carbon chain. In some preferred embodiments, the hydroxyl group can be in a terminal position on the carbon chain.

Table 2 shows the water solubility for traditional parabens, as taken from ISCA UK Ltd. The water solubility of various parabens ranges from 0.02%-0.25%, worse than benzoic acid. Not surprisingly, the solubility of the parabens decrease as the chain length increases. The low water solubility of parabens limits their use to low concentrations in cosmetic and personal care products. Additionally, the low water solubility indicates that parabens will migrate towards the oil-phase in emulsions, and therefore, can have a reduced efficacy in these formulation types. As previously noted, parabens have also been subject to regulation and negative consumer perceptions, limiting their potential applications in various products.

TABLE 2

Solubility of Parabens in various solvents.

| | Solubility of Parabens (% w/w at 25° C.) | | | |
|---|---|---|---|---|
| Solvent | Methylparaben | Ethylparaben | Propylparaben | Butylparaben |
| Water | 0.25 | 0.11 | 0.04 | 0.02 |
| Propylene glycol | 26 | 20 | 29 | 49 |
| Ethanol | 32 | 41 | 50 | 68 |

Benzoic acid esters including a carbon chain having a hydroxyl group can serve as an antibacterial agent in compositions of the present disclosure. Various benzoic acid esters were synthesized and tested for their water solubility and pH dependence. The results of this testing are shown in Table 3.

TABLE 3

Testing results on water solubility and pH dependence for benzoic acid esters including a carbon chain and a hydroxyl group on the carbon chain.

| # | Compound Name | Compound Structure | Solubility (wt %) | pKa |
|---|---|---|---|---|
|  | benzoic acid |  | 0.30 | 4.2 |
| 8 | Benzoic acid 2-hydroxyethyl ester | 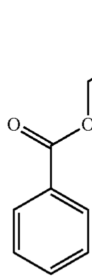 | >1.0 | >7.0 |
| 9 | Benzoic acid 2,3-dihydroxypropyl ester | 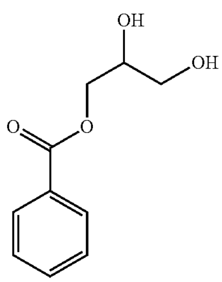 [SMILES: O=C(OCC(O)CO)c1ccccc1] | >1.0 | >7.0 |
| 10 | Benzoic acid 4-hydroxybutyl ester | 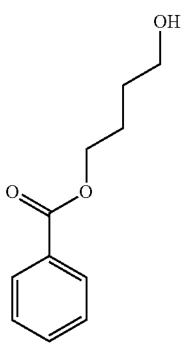 [SMILES: O=C(OCCCCO)c1ccccc1] | 0.47 | >7.0 |
| 11 | Benzoic acid 3-hydroxy-propyl ester | 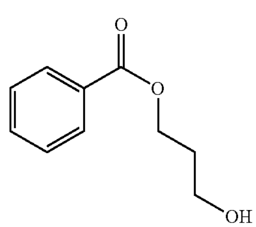 [SMILES: O=C(OCCCO)c1ccccc1] | 0.55 | >7.0 |
| 12 | Benzoic acid 2-hydroxybutyl ester | 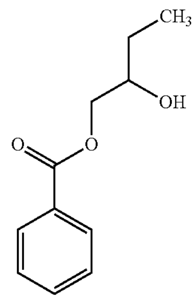 | 0.24 | >7.0 |

There are multiple advantages to the benzoic acid esters of the present disclosure in comparison to benzoic acid, specifically around water solubility and pH dependence. As shown in Table 3, esterification of the benzoic acid and synthesizing the benzoic acid ester to have a carbon chain with a hydroxyl group provides a substantial increase in water solubility as compared to benzoic acid, with the synthesized benzoic acid esters demonstrating a water solubility of 0.47% to >1% with benzoic acid only having a water solubility of 0.30%. It is believed that the increase in water solubility for the benzoic acid esters is due to the fact that the ester can hydrogen bond with water molecules; thus making the benzoic acid ester more water soluble than benzoic acid. Benzoic acid esters also have greater water solubility in comparison to traditional paraben preservatives. Table 3 shows that the water solubility for benzoic acid esters ranged from 0.47% to >1% as compared to the water solubility range of 0.02% to 0.25% of the parabens as noted in Table 2.

Additionally, the benzoic acid esters of the present disclosure as tested herein have significant advantages for pH dependence as they exhibit pKa values greater than 7.0, and as such, there is no pH dependence as with benzoic acid. This provides further versatility to the benzoic acid esters as antibacterial agents in the compositions of the present disclosure.

The benzoic acid esters of the present disclosure were also tested for their efficacy against a range of bacteria and fungi. While certain benzoic acid esters known in the art may be documented as having a preservative effect, it was uncertain whether synthesizing benzoic acid esters to have carbon chains and hydroxyl groups on the carbon chains would affect the antibacterial efficacy of such compounds. Table 4 displays the MIC values for these benzoic acid esters tested against the same bacteria and fungi that were tested against the benzoic acid derivatives including a hydroxyl, polyol or sugar that are listed in Table 1. As shown in Table 4, the benzoic acid esters having a carbon chain and a hydroxyl group on the carbon chain demonstrated good efficacy against most bacteria and fungi tested in comparison to benzoic acid. As indicated by the underlined values in Table 4, several of the tested compounds even exhibited MIC values that were less than or equal to the MIC values of benzoic acid for the same respective bacteria/fungi. While some compounds may have exhibited MIC values for certain bacteria or fungi that were greater than benzoic acid for the same respective bacteria/fungi, the tested benzoic acid esters were still efficacious against a wide variety of bacteria and still exhibit other benefits compared to benzoic acid as noted herein. Thus, the benzoic acid esters including a carbon chain with a hydroxyl group are advantageous antibacterial agents in that they demonstrate high water solubility, low pH dependence, and yet still provide efficacious MIC values against a wide variety of bacteria.

Table 4 also demonstrates the unpredictability of the efficacy of benzoic acid esters having carbon chains and hydroxyl groups on the carbon chain to serve as an antimicrobial agent against certain bacteria and fungicides. For example, compound #9 in Table 4 demonstrated poor MIC values (>1.0) against each fungi tested (*C. albicans* and *A. brasiliensis*), but demonstrated MIC efficacy values much closer to the values exhibited by benzoic acid against each bacteria tested (*S. aureus, E. coli, B. cepacia*, and *P. aeruginosa*). To the contrary, other benzoic acid esters demonstrated better efficacy against fungicides, but were less effective (higher MIC efficacy values) against bacteria.

TABLE 4

MIC and cLogP values for the benzoic acid esters of Table 3.

| | | | | MIC (%) | | | | | |
|---|---|---|---|---|---|---|---|---|---|
| # | Compound Name | Compound Structure | cLogP | *S. Aureus* | *E. coli* | *B. cepacia* | *P. aeruginosa* | *C. albicans* | *A. brasiliensis* |
| | Benzoic Acid | | — | 0.068 | 0.07 | 0.034 | 0.068 | 0.137 | 0.137 |
| 8 | Benzoic acid 2-hydroxyethyl ester | | 1.29 | 0.475 | 0.475 | 0.118 | 0.237 | 0.475 | <u>0.118</u> |
| 9 | Benzoic acid 2,3-dihydroxypropyl ester | | 0.66 | 0.25 | 0.5 | 0.25 | 0.5 | >1 | >1 |
| 10 | Benzoic acid 4-hydroxybutyl ester | | 1.86 | <u>0.057</u> | 0.115 | 0.057 | 0.115 | <u>0.115</u> | <u>0.028</u> |

TABLE 4-continued

MIC and cLogP values for the benzoic acid esters of Table 3.

| # | Compound Name | Compound Structure | cLogP | MIC (%) | | | | | |
|---|---|---|---|---|---|---|---|---|---|
| | | | | S. Aureus | E. coli | B. cepacia | P. aeruginosa | C. albicans | A. brasiliensis |
| 11 | Benzoic acid 3-hydroxy-propyl ester | 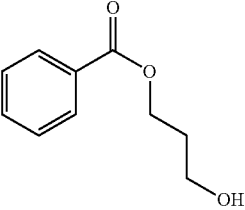 [SMILES: O=C(OCCCO)c1ccccc1] | 1.35 | 0.272 | 0.272 | 0.136 | >0.272 | 0.136 | 0.068 |
| 12 | Benzoic acid 2-hydroxy-butyl ester | 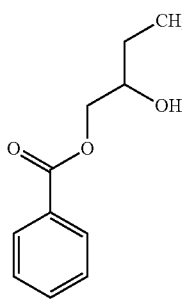 | 2.23 | 0.1175 | 0.0588 | 0.1175 | >0.1175 | 0.1175 | 0.0588 |

Table 4 also shows the calculated octanol/water partition coefficient (c Log P) of the benzoic acid esters. The c Log P values listed in Table 4 were calculated using the MarvinSketch software program, version 15.6.1.0, provided by ChemAxon Ltd. (http://chemaxon.com). The settings used to calculate c Log P within that program were: Consensus Method, Cl— concentration of 0.1 mol/dm³ and Na⁺K⁺ concentration of 0.1 mol/dm³. It is believed that the c Log P characteristic of an antibacterial agent plays a key role in determining the efficacy of that ingredient. If the c Log P value of a molecule is too low (that is, the molecule is too hydrophilic), it may not be able to cross the hydrophobic cell membrane and enter the cell. On the other hand, if the c Log P value of a molecule is too high (that is, the molecule is too hydrophobic), it can be difficult to solubilize in aqueous formulations. One key advantage of the benzoic acid esters described herein is that they are able to provide strong efficacy at relatively low c Log P values. However, within this subset of structures, it is still important to keep c Log P values within a reasonable range to maintain good efficacy and water solubility. This can be observed in compound #9, which has a calculated c Log P value of 0.66, but demonstrated a much lower broad-spectrum efficacy compared to similar structures with higher c Log P values. In a preferred embodiment, the c Log P value of the benzoic acid ester can be greater than about 0.66. More preferably, the c Log P value of a benzoic acid ester can be between about 0.67 and about 4.0. Even more preferably, the c Log P value of a benzoic acid ester is between about 0.75 and about 3.0, and still more preferably, between about 1.0 and about 2.0.

It is envisioned that various modifications can be made to benzoic acid esters demonstrating the advantages of high water solubility, low pH dependence, and efficacy against a broad spectrum of bacteria and fungi. For example, it is envisioned that benzoic acid esters could include, but are not limited to, a carbon chain length from about 2 to about 10. Preferably, benzoic acid esters of the present disclosure include a carbon chain of about 2 to about 6, as Table 3 demonstrated that as the carbon chain length is increased, the water solubility decreases. In some embodiments, the carbon chain on the benzoic acid ester can be linear. In other embodiments, however, the carbon chain on the benzoic acid ester can be non-linear.

As shown in the tested compounds, the benzoic acid esters preferably include a hydroxyl group. In some embodiments, the hydroxyl or alcohol group (OH) can exist in the terminal position of the carbon chain. In other embodiments, the hydroxyl group can exist at internal (non-terminal) positions along the carbon chain. This is seen in compound #12, which included the hydroxyl or alcohol (OH) group off the second carbon in the carbon chain length of four. Another variation that is contemplated is that more than one alcohol (OH) group could exist on the carbon chain.

Some embodiments of the antibacterial compositions of the present disclosure can be suitably made with a benzoic acid ester in an amount of from about 0.001% (by the total weight of the composition), to about 5% (by total weight of the composition), or preferably from about 0.01% (by total weight of the composition) to about 3% (by total weight of the composition), or more preferably from about 0.05% (by total weight of the composition) to about 1.0% (by total weight of the composition).

Carriers

The antibacterial compositions of the present disclosure may be formulated with one or more conventional and compatible carrier materials. The antibacterial composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic, pharmaceutical, and medical arts as a basis for ointments, lotions, creams, salves, aerosols, gels, suspensions, sprays, foams, washes, and the like, and may be used in their established levels. The carrier can comprise from about 0.01% to about 99.98% (by total weight of the composition), depending on the carrier used.

Preferable carrier materials include polar solvent materials, such as water. Other potential carriers include emollients, humectants, polyols, surfactants, esters, perfluorocarbons, silicones, and other pharmaceutically acceptable carrier materials. In one embodiment, the carrier is volatile, allowing for immediate deposition of the antibacterial ingredient to the desired surface while improving overall usage experience of the product by reducing drying time. Non-limiting examples of these volatile carriers include 5 cst Dimethicone, Cyclomethicone, Methyl Perfluoroisobutyl Ether, Methyl Perfluorobutyl Ether, Ethyl Perfluoroisobutyl Ether and Ethyl Perfluorobutyl Ether. Unlike conventional volatile carriers such as ethanol or isopropyl alcohol, these carriers have no antibacterial effect.

In one embodiment, the antibacterial compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, fatty acids, glycerol esters and derivatives, propylene glycol esters and derivatives, alkoxylated carboxylic acids, alkoxylated alcohols, fatty alcohols, and combinations thereof.

Some embodiments of the antibacterial compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In some embodiments, the antibacterial compositions include one or more esters other than benzoic acid esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. The fatty acids can include, but are not limited to, capric acid, undecylenic acid, lauric acid, Myristic acid, palmitic acid, stearic acid, oleic acid, linoleic acid, arachidic acid, and behenic acid. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the antibacterial compositions or the present disclosure are listed in the *International Cosmetic Ingredient Dictionary and Handbook,* 11th Edition, CTFA, (January, 2006) ISBN-10: 1882621360, ISBN-13: 978-1882621361, and in the 2007 *Cosmetic Bench Reference,* Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the antibacterial compositions of the present disclosure include, for example, glycerin, glycerin derivatives, hyaluronic acid, hyaluronic acid derivatives, betaine, betaine derivatives, amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof.

The antibacterial compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

The antibacterial compositions may include water. For instance, where the antibacterial composition is a wetting composition, such as described below for use with a wet wipe, the composition will typically include water. The antibacterial compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition). In some embodiments, water can comprise an amount from about 50.00% (by total weight of the composition) to about 70.00% (by total weight of the composition). In some embodiments, water can comprise an amount greater than 90.00% (by total weight of the composition).

In an embodiment where the antibacterial composition serves as a wash (e.g. shampoo; surface cleaner; or hand, face, or body wash), the antibacterial composition will likely include one or more surfactants. In an embodiment where the antibacterial composition is included in a wipe, the antibacterial composition may also likely include one or more surfactants. These may be selected from anionic, cationic, nonionic, zwitterionic, and amphoteric surfactants. Amounts of surfactants may range from 0.01 to 30%, or from 0.05 to 20%, or from 0.10 to 15% by total weight of the composition. In some embodiments, the surfactant can comprise less than 1% by total weight of the composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and trid tridecanol ethoxylates.

Suitable zwitterionic surfactants include, for example, alkyl amine oxides, alkyl hydroxysultaines, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, lauryl hydroxysultaine and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amnphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the antibacterial compositions. Suitable rheology modifiers are compatible with the antibacterial agent. As used herein, "compatible" refers to a compound that, when mixed with the antibacterial agent, does not adversely affect the antibacterial properties of same.

A thickening system is used in the antibacterial compositions to adjust the viscosity and stability of the compositions. Specifically, thickening systems prevent the composition from running off of the hands or body during dispensing and use of the composition. When the antibacterial composition is used with a wipe product, a thicker formulation can be used to prevent the composition from migrating from the wipe substrate.

The thickening system should be compatible with the compounds used in the present disclosure; that is, the thickening system, when used in combination with the antibacterial compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include but are not limited to hydroxyethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 1 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP. In embodiments where the compositions are included in a wipe, the viscosity may range from about 1 cP to about 2000 cP.

Typically, the antibacterial compositions of the present disclosure include the thickening system in an amount of no more than about 20% (by total weight of the composition), or from about 0.01% (by total weight of the composition) to about 20% (by total weight of the composition). In another aspect the thickening system is present in the antibacterial composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Emulsifiers

In one embodiment, the antibacterial compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipopiliclipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, Isosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, Ill.)); ARLACEL LC (INCI: Sorbitan Stearate (and) Sorbityl Laurate, commercially available from Croda (Edison, N.J.)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, N.J.)); UNIOX CRISTAL (INCI: Cetearyl Alcohol (and) Polysorbate 60 (and) Cetearyl Glucoside, commercially available from Chemyunion (São Paulo, Brazil)). Other suitable emulsifiers include lecithin, hydrogenated lecithin, lysolecithin, phosphatidylcholine, phospholipids, and combinations thereof.

Adjunct Ingredients

The antibacterial compositions of the present disclosure may additionally include adjunct ingredients conventionally found in cosmetic, pharmaceutical, medical, or personal care compositions/products in an established fashion and at established levels. For example, the antibacterial compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the antibacterial compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the antibacterial compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the antibacterial compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

In addition to the benzoic acid ester antibacterial agents discussed herein, the antibacterial composition may include various combinatorial preservatives/antimicrobial agents to increase shelf life. Some suitable combinatorial preservatives that may be used in the present disclosure include traditional preservatives. As used herein, "traditional preservatives" means compounds that have been historically recognized by regulatory bodies as providing preservative or antimicrobial effect, such as those listed in the European Union's Annex V list of preservatives allowed in cosmetics products. Traditional preservatives include, but are not limited to: propionic acid and salts thereof; salicylic acid and salts thereof; sorbic acid and salts thereof; benzoic acid and salts and esters thereof; formaldehyde; paraformaldehyde; o-phenylphenol and salts thereof; zinc pyrithione; inorganic sulfites; hydrogen sulfites; chlorobutanol; benzoic parabens, such as methylparaben, propylparaben, butylparaben, ethylparaben, isopropylparaben, isobutylparaben, benzylparaben, sodium methylparaben and sodium propylparaben; dehydroacetic acid and salts thereof; formic acid and salts thereof; dibromohexamidine isethionate; thimerosal; phenylmercuric salts; undecylenic acid and salts thereof; hexetidine; 5-bromo-5-nitro-1,3-dioxane; 2-bromo-2-nitropropane-1,3-diol; dichlorobenzyl alcohol; triclocarban; p-chloro-m-cresol; triclosan; chloroxylenol; imidazolidinyl urea; polyaminopropyl biguanide; phenoxyethanol, methenamine; quaternium-15; climbazole; DMDM hydantoin; benzyl alcohol; piroctone olamine; bromochlorophene; o-cymen-5-ol; methylchloroisothiazolinone; methylisothiazolinone; chlorophene; chloroacetamide; chlorhexidine; chlorhexidine diacetate; chlorhexidine digluconate; chlorhexidine dihydrochloride; phenoxyisopropanol; alkyl (C12-C22) trimethyl ammonium bromide and chlorides; dimethyl oxazolidine; diazolidinyl urea; hexamidine; hexamidine diisethionate; glutaral; 7-ethylbicyclooxazolidine; chlorphenesin; sodium hydroxymethylglycinate; silver chloride; benzethonium chloride; benzalkonium chloride; benzalkonium bromide; benzylhemiformal; iodopropynyl butylcarbamate; ethyl lauroyl arginate HCl; citric acid and silver citrate.

Other combinatorial preservatives that may be added to the antibacterial compositions of the present disclosure include non-traditional preservatives that are known to exhibit antimicrobial effects in addition to their primary functions, but that have not historically been recognized as preservatives by regulatory bodies (such as on the European Union's Annex V list). Examples of these non-traditional antimicrobial ingredients include, but are not limited to, hydroxyacetophenone, caprylyl glycol, sodium coco-PG dimonium chloride phosphate, phenylpropanol, lactic acid and salts thereof, caprylhydroxamic acid, levulinic acid and salts thereof, sodium lauroyl lactylate, phenethyl alcohol, sorbitan caprylate, glyceryl caprate, glyceryl caprylate, ethylhexylglycerin, p-anisic acid and salts thereof, gluconolactone, decylene glycol, 1,2-hexanediol, glucose oxidase and lactoperoxidase, *leuconostoc*/radish root ferment filtrate and glyceryl laurate.

The amount of the combinatorial preservatives/antibacterial agents in the antibacterial compositions is dependent on the relative amounts of other components present within the composition. For example, in some embodiments, the combinatorial preservative is present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition). In some embodiments, the combinatorial preservative can be present in the composition in an amount less than 0.2% (by total weight of the composition).

However, in some embodiments, the antibacterial composition is substantially free of any combinatorial preservative, yet still provides adequate efficacy against bacterial growth. Thus, in some embodiments, the antibacterial composition does not include a traditional preservative or a non-traditional preservative.

Delivery Vehicles

The antibacterial compositions of the present disclosure may be used in combination with a product that can serve as a delivery vehicle for the antibacterial composition. For example, the antibacterial composition may be incorporated into or onto a substrate, such as a wipe substrate, an absorbent substrate, a fabric or cloth substrate, a tissue or paper towel substrate, or the like. In one embodiment, the antibacterial composition may be used in combination with a wipe substrate to form a wet wipe or may be a wetting composition for use in combination with a wipe which may be dispersible. In other embodiments, the antibacterial composition may be incorporated into wipes such as wet wipes, hand wipes, face wipes, cosmetic wipes, cloths and the like. In yet other embodiments, the antibacterial compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an aqueous solution termed the "wetting composition," which may include or be composed entirely of the antibacterial compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

Exemplary Syntheses of Benzoic Acid Esters

The following methods are exemplary synthesis methods of select benzoic acid esters of the present disclosure.

Compound #8: Benzoic Acid 2-Hydroxy-Ethyl Ester
Scheme:

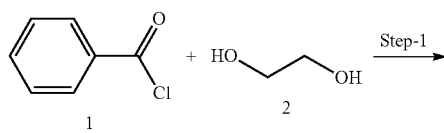

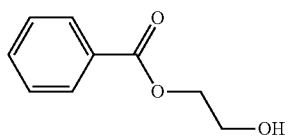

Experimental Procedure:

Step-1:

To a stirred solution of benzoyl chloride (10 g, 71.13 mmol) in pyridine (50 mL) was added DMAP (4-dimethyl-amino-pyridine) (173 mg, 1.42 mmol) and cooled at 0 to 5° C. for 15 min. To this, ethylene glycol (4.3 mL, 78.24 mmol) was added drop-wise and stirred for 4 h at 0 to 5° C. After completion of reaction (by TLC), the reaction mixture was diluted with water (100 mL) and was extracted with ethyl acetate (2×75 mL). The combined organic layer was dried over sodium sulfate and evaporated under vacuum to obtain crude product. Purification of the crude product using column chromatography (silica gel, ethyl acetate/hexane as eluent) afforded 5.5 g of Benzoic acid 2-hydroxy-ethyl ester as a pale brown liquid.

An alternate scheme for the synthesis of this molecule has also been performed as shown below:

Experimental Procedure:

Step-1:

To a solution of ethylene glycol (12.36 g, 0.2 mol) in dichloromethane (140 mL) was added trimethylamine (41.4 mL, 0.3 mol) and benzoyl chloride (14.0 g, 0.1 mol) at ice bath temperature. The reaction mixture was stirred at room temperature over a period of 60 min.

The resulting reaction mass was diluted with ethyl acetate (750 mL), washed with water (2×100 mL) and the ethyl acetate layer was dried over sodium sulfate. The crude product obtained upon evaporation of volatiles under reduced pressure was purified by silica gel flash column chromatography using ethyl acetate/hexane as an eluent to obtain benzoic acid 2-hydroxy-ethyl ester as viscous oil (6.0 g, 34%).

Compound #9: Benzoic Acid 2,3-Dihydroxypropyl Ester

Scheme:

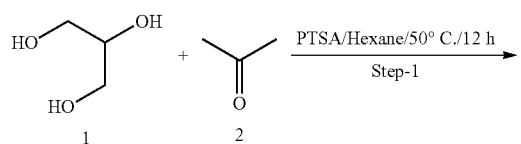

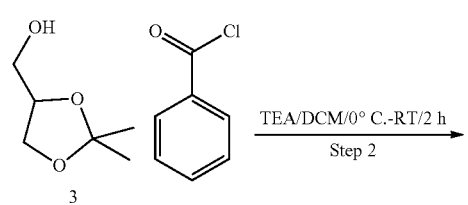

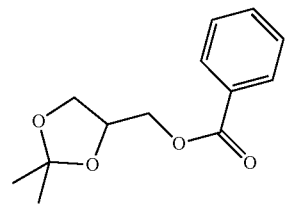

Step-3 | 2N HCl/THF/45° C./1 h

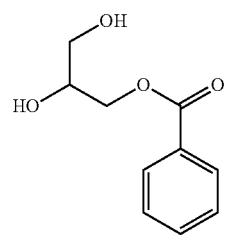

Experimental Procedure:

Step-1:

A mixture of Glycerol (15 g, 0.16 mol), acetone (45 ml), PTSA (0.5 g) and hexanes (45 ml) were heated at 60° C. for 12 h. Water formed during the course of reaction was removed over Dean-Stark equipment. A non-polar spot were formed (TLC visualization:KMNO4). The reaction was quenched by adding with NaOAc (0.45 g). After stirring for an additional 30 min at RT, the organic layer was concentrated under vacuum to result in crude Intermediate-3. The crude was purified through high vacuum (5 mmHg) distillation and fraction was collected at 70° C. This resulted in 14 g of pure Intermediate-3 as colorless oil.

Intermediate-3 (7 g, 0.05 mol) alcohol was dissolved in dichloromethane (DCM) (70 mL) and cooled to 0-5° C., Triethyl amine (TEA) (11 mL, 0.079 mol) was added and stirred for 15-20 min. This was followed by slow addition of benzoyl chloride (7.5 g, 0.054 mol) over a period of 10 min. Stirring was continued for an additional 1 hour at 0-5° C. The reaction was monitored by TLC. After completion of the reaction, the reaction mixture was diluted with DCM (70 mL) and washed with water (3×50 mL). The organic layer was dried over $Na_2SO_4$ and concentrated under vacuum. This resulted in 12 g of pure intermediate-4. It was used in the next step without further purification.

Intermediate-4 (10 g, 0.04 mol) was dissolved in THF (50 mL), and to this solution 2N HCl (2 mL) was added at 0-5° C. Stirring was continued for 10 min and the reaction was further heated to 50° C. for 1.5 h. After completion of reaction, the reaction mass was concentrated under reduced pressure and the crude product was purified by column chromatography (silica gel 230-400) using Etylt Acetate-Hexane. Purification resulted in 5 g of pure Compound #9 with HPLC purity of about 95%.

Compound #10: Benzoic Acid 4-Hydroxy-Butyl Ester
Scheme:

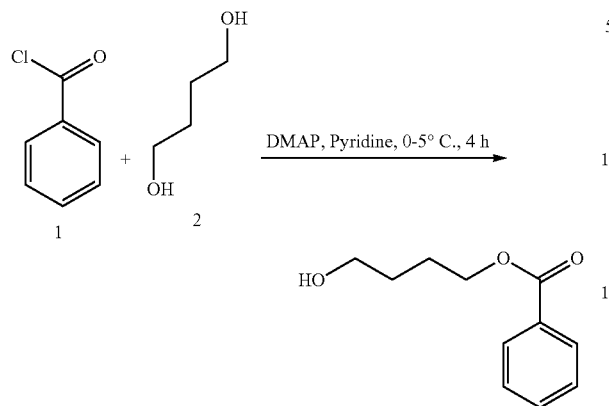

Experimental Procedure:

To a stirred solution of benzoyl chloride 1 (10 g, 0.0711 mol) in pyridine (50 mL) was added DMAP (4-dimethyl-amino-pryidine) (173 mg, 1.42 mmol) and cooled to 0-5° C. To this chilled solution, alcohol 2 (7.5 mL, 0.085 mol) was added drop-wise and stirred for 4 h between 0-5° C. After completion of reaction, the reaction mixture was diluted with water (100 mL) and was extracted into ethyl acetate (2×75 mL). The combined organic layer was dried over sodium sulfate and the solvent was removed under vacuum to obtain crude product. The crude product was purified by flash column chromatography using silica gel. (Eluent: ethyl acetate/hexane). The required product elutes at around 40% ethyl acetate-hexane. Purification afforded 5.5 g of benzoic acid 4-hydroxy-butyl ester as a brown liquid.

Compound #11: Benzoic Acid 3-Hydroxy-Propyl Ester
Scheme:

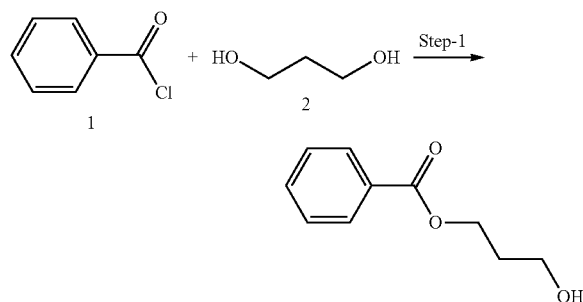

Experimental Procedure:
Step-1:

To a solution of propane-1,3-diol 2 (8.1 g, 0.106 mol) in dichloromethane (75 mL) was added trimethylamine (22.0 mL, 0.16 mol) and benzoyl chloride (7.5 g, 0.053 mol) at ice bath temperature. The reaction mixture was stirred at room temperature over a period of 30 min.

The resulting reaction mass was diluted with ethyl acetate (250 mL), washed with water (2×50 mL) and the ethyl acetate layer was dried over sodium sulfate. The crude product obtained upon evaporation of volatiles under reduced pressure was purified by silica gel flash column chromatography using ethyl acetate/hexane as an eluent to obtain the benzoic acid 3-hydroxy-propyl ester as viscous oil (5.0 g, 52%).

Compound #12: Benzoic Acid 2-Hydroxy-Butyl Ester
Scheme:

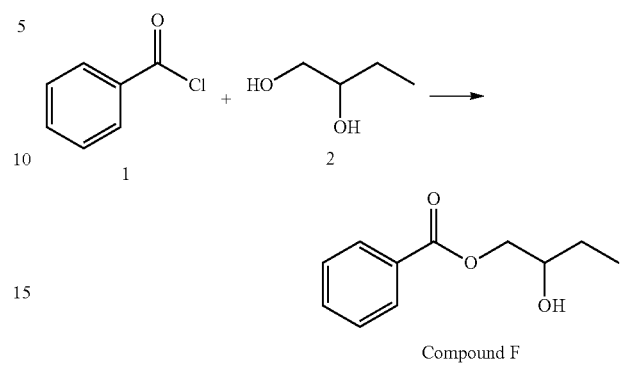

Compound F

Experimental Procedure:
Step-1:

To a solution of butane-1,2-diol 2 (20.0 g, 0.22 mol) in toluene (100 mL) was added trimethylamine (155 mL, 1.11 mol) and benzoyl chloride (155.0 g, 1.11 mol) at ice bath temperature. The reaction mixture was stirred at 140° C. over a period of 7 min. Reaction mixture was filtered to remove insoluble and concentrated under reduced pressure. The crude product obtained upon evaporation of volatiles under reduced pressure was purified by silica gel flash column chromatography using ethyl acetate/hexane as an eluent to obtain the benzoic acid 2-hydroxy-butyl ester as a pale yellow oil (6.5 g, 15%).

Test Methods

Determination of Aqueous Solubility (pH-4.5) by Miniaturized Shake Flask Method
  Test Media: Ultrapure water (pH-4.5) (18 MΩ DI water)
  Test Concentration: 10 mg/ml
  Incubation Details: 22° C.+/−3° C.
  Method of Analysis: Photometric analysis using Microplate reader, CL-MS/MS (Compound #12)
  Data Output: Aqueous Solubility
  Study Procedure:

Preparation of 0.1 M Citric Acid Monohydrate Solution

Approximately, 1.050 g of citric acid monohydrate was weighed and dissolved in 50 mL of ultrapure water. The solution was transferred to 50 mL tube and stored at room temperature (22° C.±3° C.).

Preparation of 0.1 M Trisodium Citrate Solution

Approximately, 1.471 g of trisodium citrate was weighed and dissolved in 50 mL ultrapure water and stored at room temperature (22° C.±3° C.).

Preparation of Citrate Buffer Solution (pH-4.5)

47 mL of 0.1 M citric acid monohydrate solution and 53 mL of trisodium citrate solution was mixed. pH of the solution was found to be 4.50.

Preparation of Ultrapure Water (pH-4.5)

Required volume of ultrapure water (~75 mL) was taken and pH was adjusted to 4.5 using citrate buffer (pH-4.5).

This water was used as a test media for determining the solubility of test/reference items.

Preparation of Stock Solution

Stock solutions of concentration 1 mg/mL for test items/reference items was prepared in methanol. The stock solution will be used for preparation of calibration curve standards.

Preparation of Calibration Curve

Calibration curve of test/reference items was prepared by serially dilution consisting of 4-5-6 concentrations in 96 well format. Standard concentrations of 500 µg/mL, 200 µg/mL, 50 µg/mL, 12.5 µg/mL and 3.125 µg/mL (and 0.781 µg/mL for Compound #8 benzoic acid 2-hydroxy-ethyl ester) were included.

Methanol stock solution of 1 mg/mL concentration was prepared for test/reference items.

The initial concentration of 500 µg/mL was prepared by adding 112.5 µL from a stock solution of 1 mg/mL to first well of a 96 well plate in duplicates and diluted with 112.5 µL of Ultrapure water. NOTE: Only a concentration of 200 µg/mL was prepared for Compound #8 benzoic acid 2-hydroxy-ethyl ester.

Similarly, a concentration of 200 µg/mL was prepared by adding 60 µL of 1 mg/mL methanol stock, 90 µL of methanol, 150 µL of Ultrapure water (pH-4.5) to the following wells in duplicates.

To the rest of the wells, 225 µL of vehicle (methanol: ultrapure water; 50:50) was added. 75 µL of 200 µg/mL solution was serially diluted.

The last two wells of each row was considered as blank.

The plate was incubated 22° C.±3° C. and 300 rpm for 30 minutes.

After incubation 100 µL of the incubated sample was transferred to an UV plate for UV analysis.

The plate was scanned from 200-400 nm to obtain $A_{max}$ (absorbance maximum) wavelength, λmax.

For Compound #12, the calibration curve was determined in a similar way, but with slight differences. The method was as follows:

Calibration curve of test items were prepared by serial dilution consisting of 8 concentrations. Standard concentrations of 50 µg/mL, 12.5 µg/mL, 3.125 µg/mL, 0.781 µg/mL, 0.195, 0.048, 0.012 and 0.003 µg/mL were prepared using dilution solvent (Methanol: Water, 50:50).

200 µL of calibration standards were transferred to auto sampler vials and submitted for LC-MS/MS analysis.

Solubility Testing by Shake Flask Method

The solubility of test items were determined at a highest test concentration of 1% w/v (10 mg/mL).

40 mg of test items were weighed into tubes.

4 mL of Ultrapure water was added to all tubes to get a concentration of 10 mg/mL (1% w/v).

The initial pH of the solubility samples were recorded. Then the pH of the solubility samples were adjusted to 4.5 using citrate buffer and vortexed. Then, the solutions were observed visually for any precipitation.

After adjusting pH to 4.5, the test items which were found to be insoluble were diluted further with water and observed for solubility ensuring that the pH of the water is maintained at 4.5 until solubility (no visual precipitation) was observed.

The visually soluble samples were centrifuged at 10000 rpm for 10 minutes at room temperature (22° C.±3° C.).

An aliquot of the supernatant were diluted with equal volume of methanol. The samples were further diluted in methanol: water (50:50) to obtain dilution of 1:2, 1:4, 1:16, 1:32 etc.

The samples were then transferred to UV plate and scanned at $\lambda_{max}$ of that particular test/reference item. Compound #12 was transferred to auto-sampler vials and submitted for LC-MS/MS analysis.

Determination of Dissociation Constant (pKa) by Potentiometric Titration Method

Test Media: Ultrapure water (pH-4.5) (18 MΩ DI water)
Test Concentration: 0.1 mg/ml
Incubation Details: 22° C.+/−0.5° C.
Method of Analysis: Potentiometric Titration using pH Meter
Data Output: Dissociation constant, pKa
Study Procedure:

Preparation of 1.0 N HCl Solution 40 mL of Ultrapure water was taken in measuring cylinder. To it, 4.41 mL of 35% pure HCl was added. The volume was then be made up to 50 mL using Ultrapure water. The solution was transferred to 50 mL tube and stored at room temperature (22° C.±3° C.).

Preparation of 0.1 N HCl Solution 5 mL of 1 N HCl solution was diluted to 50 mL and stored in tubes at 22° C.±3° C. until use.

Preparation of 1.0 N NaOH Solution 2 g of Sodium hydroxide pellets were weighed and transferred to a tube. The pellets was dissolved in 50 mL of Ultrapure and stored at room temperature (22° C.±3° C.).

Preparation of 0.1 N NaOH Solution 5 mL of 1 N NaOH solution was diluted to 50 mL and stored in tubes at 22° C.±3° C. until use.

Preparation of Test Solution

Test solutions of test items/reference items was prepared in Ultrapure water at a concentration of 100 µg/mL.
Potentiometric Titration Method:
A calibrated pH meter was used for the assay.
50 mL solution of each test/reference item solution (0.1 mg/mL) was added to four beakers (two for acid titration and two for base titration).
0.1 N Sodium hydroxide (NaOH) solution was prepared as titrant solution.
The pH electrode was placed into the beaker containing test/reference item solution.
The initial pH of the solution will be recorded. 100 µL of 0.1 N NaOH was added successively with stirring and the pH at each addition was recorded.
Base titrations were carried out individually in duplicates until a sudden shift in the pH was observed.
The volumes of 0.1 N NaOH consumed was plotted against the pH recorded to determine the equivalence point and pKa value.

Anti-Bacterial and Anti-Fungal Minimum Inhibitory Concentration (MIC) Method
Method: Microbroth Dilution Method (96-well format).

Test item: Compound #8 (benzoic acid 2-hydroxy-ethyl ester), Compound #9 (benzoic acid 2,3-dihydroxypropyl ester), Compound #10 (benzoic acid 4-hydroxy-butyl ester), Compound #11 (benzoic acid 3-hydroxy-propyl ester), Compound #12 (benzoic acid 2-hydroxy-butyl ester)

Testing concentration:
☐Test Compound #8: 0.019 to 9.5 mg/mL
☐Test Compound #9: 0.02 to 10.0 mg/mL
Test Compound #10: 0.004 to 2.3 mg/mL
Test Compound #11: 0.005 to 2.723 mg/mL
☐Test Compound #12: 1.175 to 0.0023 mg/mL
Solvent: Sterile MilliQ water and 0.1 M Citrate Buffer pH 4.5
Media used:
Bacterial: Cation-Adjusted Mueller-Hinton Broth (CAMHB)
Fungi: RPMI-1640
Bacteria
☐Incubation Temperature: 37° C.
☐Incubation Time: 24 hours
☐Inoculum Size: 5×10(5) cfu/mL
Strains:
  Staphylococcus aureus (ATCC 6538)
  Escherichia coli (ATCC 8739)
  Pseudomonas aeruginosa (ATCC 9027)
  Burkholderia cepacia (ATCC 25416)
Fungi:
Incubation Temperature:
  25° C. (Candida albicans)
  35° C. (Aspergillus brasiliensis)
Incubation Time: 48 hours
Inoculum Size: 5×10$^4$ cfu/mL
Strains:
  Candida albicans (ATCC 10231)
  Aspergillus brasiliensis (ATCC 16404)
End point: Inhibition of growth, Spectrophotometer Reading @ 600 nm
Reference standards: Benzoic acid, Ciprofloxacin (for bacteria) & Fluconazole (for fungi)
QC strains
  Escherichia coli (ATCC 25922) tested against Ciprofloxacin
  Candida parapsilosis (ATC 22019) tested against Fluconazole
Test Compound Preparation:
  Initially, a 10 mg/mL concentration of each test compound was prepared with MilliQ water and pH was checked. pH was adjusted for all compounds to 4.5 with citrate buffer (pH 4.5). All solubilized and pH 4.5-adjusted test compounds were filter-sterilized before subjecting to MIC study. Benzoic acid (positive control) was also dissolved in the similar way. For MIC an aliquot of 200 µL from the above stock was dispensed into 96-well plate and further 1:1 diluted.
Maintenance of strain:
  Tester strains listed above were retrieved from −80° C. freezer and were thawed out. All the strains were inoculated on their respective agar medium and incubated under conditions/durations detailed above.
Preparation of inoculum:
  The bacterial colony suspension in 0.85% saline was adjusted to 1 McFarland's standard using Densimat which was further diluted to 1:100 in CAMHB. The fungal suspension for inoculation was prepared in 0.85% saline from 6 days old culture (for mold, A. brasiliensis) and from 2 days old culture (for yeast, C. albicans) from Sabouraud Dextrose agar medium. Culture was scrapped/scooped from the plate, suspended in saline and the spores/cells counted using haemocytometer to provide a final inoculum of 5×10$^4$ cfu/mL.

96-well Plate Preparation:
  Minimum inhibitory concentration (MIC) is performed to determine potency of test compounds along with standard antibiotics against bacterial strains. Micro titer plates were prepared as per the CLSI recommendations. One hundred and seventy five microliters of Cation-adjusted Muller Hinton Broth (CAMHB) was added to the first column of a 96 well flat bottom plate, which is the media control. Second column is for the stocks of the test compounds and reference standards from which dilutions are made. Then 175 µL of CAMHB was added to the 5th, 8th and 11th columns, 75 µL of CAMHB to the 4th, 7th and 10th columns and 50 µL of CAMHB to the 3rd, 6th and 9th columns and the last column was the organism control.

EMBODIMENTS

Embodiment 1

A method for inhibiting bacterial growth in a product, the method comprising: providing an antibacterial composition including an antibacterial agent, the antibacterial agent comprising a benzoic acid ester with a carbon chain having a length of two to ten, the benzoic acid ester further comprising a hydroxyl group on the carbon chain; and applying the antibacterial composition to the product to inhibit bacterial growth in the product.

Embodiment 2

The method of embodiment 1, wherein hydroxyl group is in the terminal position of the carbon chain.

Embodiment 3

The method of embodiment 1 or 2, wherein the antibacterial composition further comprises a carrier and a surfactant.

Embodiment 4

The method of embodiment 3, wherein the carrier comprises between about 50% and about 70% of the antibacterial composition by weight of the antibacterial composition.

Embodiment 5

The method of embodiment 3, wherein the carrier comprises at least about 90% of the antibacterial composition by weight of the antibacterial composition.

Embodiment 6

The method of any one of embodiments 3-5, wherein the surfactant comprises less than about 30% of the antibacterial composition by weight of the antibacterial composition.

Embodiment 7

The method of any one of the preceding embodiments, wherein the antibacterial composition further comprises a humectant.

Embodiment 8

The method of any one of the preceding embodiments, wherein the antibacterial composition further comprises a combinatorial preservative.

Embodiment 9

The method of any one of the preceding embodiments, wherein the benzoic acid ester comprises a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans*, and *Aspergillus brasiliensis*.

Embodiment 10

The method of any one of the preceding embodiments, wherein the product is a wipe.

Embodiment 11

An antibacterial composition comprising: a carrier; a surfactant; and an antibacterial agent, the antibacterial agent comprising a benzoic acid ester, the benzoic acid ester having a carbon chain and a terminal hydroxyl group on the carbon chain.

Embodiment 12

The antibacterial composition of embodiment 11, wherein the carrier comprises between about 50% and about 70% of the antibacterial composition by weight of the antibacterial composition.

Embodiment 13

The antibacterial composition of embodiment 11, wherein the carrier comprises at least about 90% of the antibacterial composition by weight of the antibacterial composition.

Embodiment 14

The antibacterial composition of any one of embodiments 11-13, wherein the surfactant comprises less than about 10% of the antibacterial composition by weight of the antibacterial composition.

Embodiment 15

The antibacterial composition of any one of embodiments 11-14, wherein the antibacterial composition further comprises a combinatorial preservative.

Embodiment 16

The antibacterial composition of any one of embodiments 11-15, wherein the benzoic acid ester comprises a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans*, and *Aspergillus brasiliensis*.

Embodiment 17

A wipe comprising: a substrate, and the antibacterial composition according to any one of embodiments 11-16.

Embodiment 18

An antibacterial composition comprising: a carrier; a surfactant; and an antibacterial agent, the antibacterial agent comprising a benzoic acid ester including a carbon chain and a hydroxyl group on the carbon chain; the benzoic acid ester comprising a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans*, and *Aspergillus brasiliensis*, and the antibacterial composition being substantially free of a traditional preservative.

Embodiment 19

The antibacterial composition of embodiment 18, wherein the hydroxyl group is in the terminal position of the carbon chain.

Embodiment 20

The antibacterial composition of embodiment 18 or 19, wherein the carbon chain includes a length of two to ten.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A method for inhibiting bacterial growth in a product, the method comprising:
   providing an antibacterial composition including an antibacterial agent, the antibacterial agent comprising a benzoic acid ester, wherein the benzoic acid ester is benzoic acid 2-hydroxybutyl ester; and
   applying the antibacterial composition to the product to inhibit bacterial growth in the product.

2. The method of claim 1, wherein the antibacterial composition further comprises a carrier and a surfactant.

3. The method of claim 2, wherein the carrier comprises between about 50% and about 70% of the antibacterial composition by weight of the antibacterial composition.

4. The method of claim 2, wherein the carrier comprises at least about 90% of the antibacterial composition by weight of the antibacterial composition.

5. The method of claim 2, wherein the surfactant comprises less than about 30% of the antibacterial composition by weight of the antibacterial composition.

6. The method of claim 1, wherein the antibacterial composition further comprises a humectant.

7. The method of claim 1, wherein the antibacterial composition further comprises a combinatorial preservative.

8. The method of claim 1, wherein the product is a wipe.

9. An antibacterial composition comprising:
a carrier;
a surfactant; and
an antibacterial agent, the antibacterial agent comprising a benzoic acid ester, wherein the benzoic acid ester is benzoic acid 2-hydroxybutyl ester.

10. The antibacterial composition of claim 9, wherein the carrier comprises between about 50% and about 70% of the antibacterial composition by weight of the antibacterial composition.

11. The antibacterial composition of claim 9, wherein the carrier comprises at least about 90% of the antibacterial composition by weight of the antibacterial composition.

12. The antibacterial composition of claim 9, wherein the surfactant comprises less than about 10% of the antibacterial composition by weight of the antibacterial composition.

13. The antibacterial composition of claim 9, wherein the antibacterial composition further comprises a combinatorial preservative.

14. A wipe comprising:
a substrate, and
the antibacterial composition according to claim 9.

15. An antibacterial composition comprising:
a carrier;
a surfactant; and
an antibacterial agent, the antibacterial agent comprising a benzoic acid ester, wherein the benzoic acid ester is benzoic acid 2-hydroxybutyl ester;
the antibacterial composition being substantially free of a traditional preservative.

* * * * *